United States Patent [19]

Ogawa

[11] 4,042,623
[45] Aug. 16, 1977

[54] METHOD OF MANUFACTURING METHACRYLIC ACID AND AN OXIDATION CATALYST

[75] Inventor: Masanobu Ogawa, Takasaki, Japan

[73] Assignee: Nippon Kayaku Kabushiki Kaisha, Tokyo, Japan

[21] Appl. No.: 613,921

[22] Filed: Sept. 16, 1975

[30] Foreign Application Priority Data

Sept. 24, 1974 Japan .................................. 49-108889
Sept. 24, 1974 Japan .................................. 49-108890

[51] Int. Cl. ........................... C07C 51/32; B01J 27/14
[52] U.S. Cl. ................................ 260/530 N; 252/435; 252/437
[58] Field of Search ............................. 252/435, 437; 260/530 N, 530 R

[56] References Cited

U.S. PATENT DOCUMENTS

| 2,438,164 | 3/1948 | Harrington et al. | 252/437 X |
|---|---|---|---|
| 3,087,964 | 4/1963 | Koch et al. | 252/435 X |
| 3,541,143 | 11/1970 | Nakano et al. | 252/437 X |
| 3,646,127 | 2/1972 | Akiyama et al. | 252/435 X |
| 3,792,086 | 2/1974 | Frank et al. | 252/437 X |
| 3,875,220 | 4/1975 | White et al. | 252/437 X |

Primary Examiner—Patrick P. Garvin
Assistant Examiner—William G. Wright
Attorney, Agent, or Firm—Lane, Aitken, Dunner & Ziems

[57] ABSTRACT

A catalyst for the oxidation of methacrolein into methylacrylic acid in the presence of steam having the composition:

$$Pd_aP_bSb_cX_dO_e$$

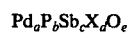

wherein, Pd, P, Sb and O denote palladium, phosphorus, antimony and oxygen respectively, X denotes at least one element selected from the group consisting of bismuth, lead, chromium, iron, nickel, cobalt, manganese, tin, uranium and barium, the subscripts $a$, $b$, $c$, $d$ and $e$ denote the numbers of the Pd, P, Sb, X and O atoms, with the proviso that the elements are present in a ratio so that when $a$ is 1, $b$ is 1 to 42, $c$ is 0.1 to 15, $d$ is 0 to 15 and $e$ is a value which is automatically determined from the valencies of the other elements.

10 Claims, No Drawings

METHOD OF MANUFACTURING METHACRYLIC ACID AND AN OXIDATION CATALYST

BACKGROUND

1. Field of the Invention

This invention relates to a method of manufacturing methacrylic acid by the oxidation of methacrolein and to an oxidation catalyst.

More particularly, this invention relates to a method of manufacturing methacrylic acid by oxidizing methacrolein with molecular oxygen or a gas containing molecular oxygen in the presence of steam, characterized by using a catalyst containing (1) palladium, (2) phosphorus, (3) antimony and (4) oxygen as the essential components and (5) at least one member selected from the group consisting of bismuth, lead, chromium, iron, nickel, cobalt, manganese, tin, uranium and barium as the optional component, and to oxidation catalyst.

2. Description of the Prior Art

Numerous catalysts have heretofore been proposed for use in the synthesis of methacrylic acid to be accomplished by the oxidation of methacrylein in a gaseous phase.

Many of these catalysts prove to be deficient in activity. When the reaction using such catalyst is carried out at an elevated temperature in the hope of enhancing the total conversion, a decomposition reaction is encountered giving rise to large volumes of undesirable by-products such as carbon monoxide and carbon dioxide. Thus, the conversion yield of methacrylic acid is low. The catalysts which are disclosed in Japanese Patent Laid Open Publication No. 67216/1973 and Japanese Patent Laid Open Publication No. 61416/1973 and which provide relatively high activity and selectively, for example, contain phosphomolybdic acid or a salt thereof as the principal component.

Phosphomolybdic acid-based catalysts have a disadvantage in that the catalyst lifetime is short. Once they lose activity, these catalysts cannot be restored to activity through a simple treatment such as re-calcination. When the temperature of reaction or calcination exceeds 450° C, they are abruptly degraded in catalytic activity, they are thermally unstable and thus, they are not necessarily suitable for use as catalysts on a commercial basis.

Further, conventional phosphomolybdic acid-based catalysts offer a notably short catalytic lifetime when the reaction is carried out at a particularly high space velocity.

From a commercial point of view, development of a catalyst capable of providing high reactivity and high selectivity at low temperatures and enjoying a long service life is highly desirable. Particularly desirable is the development of a catalyst which enjoys a long service life even when the reaction is carried out at a high space velocity.

SUMMARY OF THE INVENTION

The present invention provides a catalyst which is improved so as to overcome the drawbacks suffered by the conventional catalysts and which provides a high conversion of methacrolein, produces methacrylic acid with high selectivity, enjoys a long catalytic lifetime even at a low reaction temperature and has a long active life even when the reaction is carried out at a high space velocity.

In the manufacture of methacrylic acid by the catalytic oxidation of methacrolein in the gaseous phase at an elevated temperature, the catalyst of the present invention exhibits high activity and high selectivity, serving to inhibit formation of by-products such as acetic acid, carbon monoxide, carbon dioxide, etc. produced by a decomposition reaction. Further the catalyst increases the total conversion of methacrolein at low temperatures, enhances the yield of methacrylic acid and enjoys a notably long service life. The long service life of the catalyst is not affected even when the reaction is carried out at an unusually high space velocity.

Furthermore, the catalyst of the present invention functions stably at a high temperature such as 600° C, for example.

The catalyst which is preferred in the present invention has the following composition:

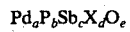

$$Pd_aP_bSb_cX_dO_e$$

wherein, Pd, P, Sb and O denote palladium, phosphorus, antimony and oxygen, respectively, X denotes at least one element selected from the group consisting of bismuth, lead, chromium, iron, nickel, cobalt, manganese, tin, uranium and barium, the subscripts $a$, $b$, $c$, $d$ and $e$ denote the numbers of the Pd, P, Sb, X and O atoms and, where $a$ is assigned a value of 1, then $b$ has a value in the range of from 1 to 42, $c$ a value in the range of from 0.1 to 15, $d$ a value in the range of from 0 to 15 and $e$ a value which is automatically determined from the valencies of the other elements involved herein and which usually falls in the range of from 3 to 120. The catalyst is more desirable when the composition thereof is such that the subscripts stand for the following relative values: $a : b : c : d : e = 1 : 1-28 : 0.3-10 : 0-10 : 5-85$. Of the possible elements denoted by X, bismuth, lead and barium are especially preferred.

DESCRIPTION OF THE PREFERRED EMBODIMENTS

In the method of the present invention a gas containing molecular oxygen is catalytically reacted with methacrolein. Air is generally adopted for this purpose. The air may be used diluted with a gas such as nitrogen or carbon dioxide which has no adverse effect upon the reaction.

The molar ratio of methacrolein and oxygen in the raw feed gas is desired to fall in the range of 1 : 0.5–30, preferably 1 : 1–8.

For the method of the present invention, presence of steam in the reaction system is indispensable. In the absence of steam, the oxidation of methacrolein proceeds only slightly. It is in this respect that the catalyst of the present invention is altogether different from any known catalyst used for the oxidation of methacrolein.

The amount of steam to be contained in the raw feed gas is desired to be in the range of from 0.5 to 40 moles, more preferably from 1 to 28 moles, per mole of methacrolein.

For the preparation of the catalyst according to this invention, any of the generally known methods available for the manufacture of catalysts of this type can be adopted.

The catalyst of this invention can be prepared, for example, as described below.

A solution containing compounds of the component elements and, where the catalyst requires use of a carrier, further containing a substance to serve as a carrier is evaporated to dryness and thereafter calcined.

Alternatively, a solid carrier is impregnated with compounds of component elements and the resultant composite is evaporated to dryness and then calcined.

Otherwise, a solid carrier is impregnated with a portion of the component elements and subjected to heat treatment at a desirable range of from 100° – 800° C and the resultant composite is impregnated with the remaining portion of compounds of component elements, evaporated to dryness and thereafter calcined.

The temperature for this calcination is desired to fall in the range of from 300° to 800° C, preferably from 350° to 550° C.

As the compounds of the individual component elements, those enumerated hereinbelow can be used, for example.

Suitable palladium compounds include palladium chloride, palladium nitrate, palladium sulfate, palladium black, etc.

Suitable phosphorus compounds include orthophosphoric acid, phosphorous acid, hypophosphorous acid, pyrophosphoric acid, meta-phosphoric acid, polyphosphoric acid and salts thereof.

Suitable antimony compounds include oxides, hydroxides and chlorides of antimony such as antimony trichloride, antimony pentachloride and antimony trioxide.

Bismuth, lead, chromium, iron, nickel, cobalt, manganese, tin, uranium and barium, compounds which can be used include nitrates, hydrochlorides, phosphates, sulfates, oxides, hydroxides, etc. of such elements.

The catalyst can include a carrier to lower the catalyst concentration, increase the catalyst strength or to enhance the economy of the catalyst.

As the carrier, there can be used an inert substance such as, for example, silica sol, silica gel, silicon carbide, α-alumina, alundum, sellaite, boiling bubble stone or aluminum powder.

In practicing the method of the present invention, the reaction temperature is desired to fall in the range of from 180° to 420° C;, preferably from 210° to 390° C.

The feed volume of the raw gas is desired to fall in the range of 300 to 15,000 lit.-gas/lit.-cat/hour, preferably 700 to 8,000 lit.-gas/lit.-cat.hour.

With the catalyst of the present invention, desirable results are obtained even when the reaction is carried out at a very high space velocity of the order of 2,000 to 8,000 lit.-gas/lit.-cat.hour. And, the catalyst of this invention still enjoys its long service life if the reaction is performed at such a high space velocity as mentioned above.

The reaction of the present invention may be carried out above or below atmospheric pressure however, it is convenient for this reaction to be carried out at a pressure approximating atmospheric pressure. The reaction pressure is preferably in the range of from 0.3 to 15 atmospheres.

The catalyst of the present invention can be used in a fixed bed, fluidized bed or moving bed.

The present invention will be described more specifically hereinbelow with reference to preferred embodiments. The conversion of methacrolein, selectivity to methacrylic acid, yield of methacrylic acid and space velocity dealt with hereinbelow are those calculated in accordance with the following definitions.

Conversion of methacrolein = (%)

$$\frac{\text{Number of moles of reacted methacrolein}}{\text{Number of moles of methacrolein in feed}} \times 100$$

Selectivity to methacrylic = acid (%)

$$\frac{\text{Number of moles of formed methacrylic acid}}{\text{Number of moles of reacted methacrolein}} \times 100$$

Yield of methacrylic = acid (%)

$$\frac{\text{Number of moles of formed methacrylic acid}}{\text{Number of moles of methacrolein in feed}} \times 100$$

Space velocity = (SV)

$$\frac{\text{Flow volume of feed gas (computed as NTP) (lit.-gas/hour)}}{\text{Volume of packed catalyst (lit.-cat.)}}$$

The yields of acrylic acid, acetic acid, carbon dioxide and carbon monoxide were calculated in accordance with the following definitions.

Yield of acrylic = acid (%)

$$\frac{\text{Number of moles of formed acrylic acid}}{\text{Number of moles of methacrolein feed}} \times 100$$

Yield acetic acid (%) =

$$\frac{\text{Number of moles of formed acetic acid}}{\text{Number of moles of methacrolein feed}} \times \frac{1}{2} \times 100$$

Yield carbon dioxide = (%)

$$\frac{\text{Number of moles of formed carbon dioxide}}{\text{Number of moles of methacrolein feed}} \times \frac{1}{4} \times 100$$

carbon monoxide = (%)

$$\frac{\text{Number of moles of formed carbon monoxide}}{\text{Number of moles of methacrolein feed}} \times \frac{1}{4} \times 100$$

EXAMPLE 1

115.8 g of silica sol was heated and agitated while, 0.71 g of antimony trioxide was added. The mixture was concentrated by heating, then evaporated to dryness and dried at 270° C for eight hours. The dried mixture was impregnated with an aqueous ammonia solution containing 0.9 g of palladium chloride, then evaporated to dryness, washed repeatedly with 10 liters of distilled water and dried. The resultant dry substance was impregnated with 5.4 g of hypophosphorous acid, evaporated to dryness and dried at 270° C for eight hours. Thereafter, the dry product was calcined in air at 450° C for four hours. The catalyst thus obtained had a composition of $Pd_1P_5Sb_1O_{15}$.

A reaction tube of stainless steel measuring 20 mm in inside diameter was packed with 40 ml of this catalyst and submerged in a bath of molten nitrate and continuously used 90 days for the oxidation reaction of methacrolein.

The raw feed gas used in the reaction consisted of methacrolein, oxygen, steam and nitrogen in a molar ratio of 1 : 4.2 : 25.3 : 16.9.

The results of the reaction were as shown in Table 1. The ratios of acrylic acid, acetic acid, carbon dioxide and carbon monoxide formed as the by-products in the conversion of methcrolein into methacrylic acid after lapse of 0 days were 7.0%, 1.3%, 7.5% and 6.5%, respectively, where SV = 1000 hr$^{-1}$.

EXAMPLES 2 – 11

By following the procedures of Example 1, catalysts having the compositions indicated in Table 1 were prepared and put to use in the direction. The results of the reaction were as shown in Table 1.

Table 1

| Ex. No. | Catalyst composition | Lapse of time (days) | SV (hr$^{-1}$) | Temperature of nitrate bath (° C) | Conversion of methacrolein (%) | Yield of methacrylic acid (%) | Selectivity to methacrylic acid (%) |
|---|---|---|---|---|---|---|---|
| 1 | $Pd_1P_5Sb_1O_{15}$ | 0 | 1000 | 290 | 72.4 | 50.1 | 69.2 |
|   |   | 0 | 4000 | 300 | 71.5 | 48.5 | 67.8 |
|   |   | 60 | 4000 | 300 | 62.3 | 42.5 | 68.2 |
|   |   | 90 | 4000 | 300 | 61.7 | 42.3 | 68.5 |
| 2 | $Pd_1P_1Sb_{0.5}O_{4.25}$ | 0 | 1000 | 267 | 76.5 | 31.5 | 41.2 |
|   |   | 0 | 4000 | 277 | 69.2 | 29.5 | 42.6 |
|   |   | 60 | 4000 | 277 | 66.5 | 27.6 | 41.5 |
|   |   | 90 | 4000 | 277 | 62.6 | 26.8 | 42.8 |
| 3 | $Pd_1P_{1.5}Sb_1O_{6.25}$ | 0 | 1000 | 275 | 75.0 | 29.9 | 39.9 |
|   |   | 0 | 4000 | 283 | 68.0 | 27.3 | 40.2 |
|   |   | 60 | 4000 | 283 | 60.2 | 25.0 | 41.5 |
|   |   | 90 | 4000 | 283 | 58.4 | 24.1 | 41.3 |
| 4 | $Pd_1P_3Sb_1O_{10}$ | 0 | 1000 | 285 | 75.5 | 46.0 | 60.9 |
|   |   | 0 | 4000 | 295 | 68.3 | 40.2 | 58.9 |
|   |   | 60 | 4000 | 295 | 60.0 | 33.8 | 56.3 |
|   |   | 90 | 4000 | 295 | 58.3 | 32.6 | 55.9 |
| 5 | $Pd_1P_{4.5}Sb_1O_{13.8}$ | 0 | 1000 | 290 | 70.3 | 49.7 | 70.7 |
|   |   | 0 | 4000 | 299 | 64.1 | 42.3 | 66.0 |
|   |   | 60 | 4000 | 299 | 56.2 | 38.1 | 67.8 |
|   |   | 90 | 4000 | 299 | 54.1 | 35.2 | 65.1 |
| 6 | $Pd_1P_6Sb_{1.5}O_{18.3}$ | 0 | 1000 | 295 | 63.5 | 45.5 | 71.6 |
|   |   | 0 | 4000 | 308 | 60.0 | 40.0 | 66.7 |
|   |   | 60 | 4000 | 308 | 52.9 | 34.4 | 65.0 |
|   |   | 90 | 4000 | 308 | 49.1 | 32.8 | 66.8 |
| 7 | $Pd_1P_5Sb_2O_{16.5}$ | 0 | 1000 | 295 | 69.3 | 49.3 | 71.1 |
|   |   | 0 | 4000 | 308 | 60.0 | 41.1 | 68.5 |
|   |   | 60 | 4000 | 308 | 53.3 | 36.8 | 69.0 |
|   |   | 90 | 4000 | 308 | 49.0 | 34.0 | 69.4 |
| 8 | $Pd_1P_5Sb_7O_{24}$ | 0 | 1000 | 310 | 60.5 | 41.1 | 67.9 |
|   |   | 0 | 4000 | 319 | 53.5 | 38.7 | 72.3 |
|   |   | 60 | 4000 | 319 | 52.6 | 35.9 | 68.3 |
|   |   | 90 | 4000 | 319 | 51.0 | 34.3 | 67.2 |
| 9 | $Pd_1P_5Sb_{10}O_{28.5}$ | 0 | 1000 | 310 | 57.8 | 37.5 | 64.9 |
|   |   | 0 | 4000 | 319 | 51.0 | 32.1 | 62.9 |
|   |   | 60 | 4000 | 319 | 45.0 | 27.6 | 61.3 |
|   |   | 90 | 4000 | 319 | 42.0 | 25.9 | 61.6 |
| 10 | $Pd_1P_7Sb_{0.5}O_{19.3}$ | 0 | 1000 | 325 | 49.5 | 30.7 | 62.0 |
|   |   | 0 | 4000 | 337 | 42.5 | 28.2 | 66.4 |
|   |   | 60 | 4000 | 337 | 39.4 | 25.6 | 65.0 |
|   |   | 90 | 4000 | 337 | 37.9 | 24.8 | 65.4 |
| 11 | $Pd_1P_{20.5}Sb_1O_{53.8}$ | 0 | 1000 | 330 | 45.2 | 27.5 | 60.8 |
|   |   | 0 | 4000 | 341 | 41.1 | 23.0 | 56.2 |
|   |   | 60 | 4000 | 341 | 39.2 | 21.3 | 54.3 |
|   |   | 90 | 4000 | 341 | 37.5 | 21.0 | 56.0 |

EXAMPLE 12

115.8 g of silica sol was heated and agitated an aqueous solution of 2.4 g of bismuth nitrate was first added and 0.7 g of antimony trioxide was further added. The mixture was concentrated by heating, then evaporated to dryness and thereafter, dried at 270° C for eight hours. The dried mixture was impregnated with an aqueous solution of ammonia containing 0.9 g of palladium chloride, evaporated to dryness, thereafter repeatedly washed with 10 liters of distilled water and dried. The dried mixture was impregnated with 5.4 g of hypophosphorous acid, evaporated to dryness and dried at 270° C for eight hours. Thereafter, the dried product was calcined in air at 450° C for four hours and put to use. The catalyst thus prepared had the following composition:

$Pb_1P_5Bi_1Sb_1O_{16.5}.$

A reaction tube of stainless steel measuring 20 mm in inside diameter was packed with 40 ml of the catalyst and submerged in a bath of molten nitrate and continuously used 90 days for the oxidation reaction of methacrolein for.

The feed gas used in the reaction consisted of methacrolein, oxygen, steam and nitrogen in a ratio of 1 : 4.2 : 25.3 : 16.9.

The results of the reaction were as shown in Table 2. The ratios of acrylic acid, acetic acid, carbon monoxide and carbon dioxide formed as the by-products in the conversion of methacrolein into methacrylic acid after lapse of 0 days were 6.0%, 1.5%, 6.7% and 7.1%, respectively, where SV = 1000 hr$^{-1}$.

EXAMPLES 13 – 50

By following the procedure of Example 12, catalysts having the compositions indicated in Table 2 were prepared and put to use in the reaction. The results were as shown in Table 2.

Table 2

| Ex. No. | Catalyst composition | Lapse of time (days) | SV (hr$^{-1}$) | Temperature of nitrate bath (°C) | Conversion of methacrolein (%) | Yield of methacrylic acid (%) | Selectivity to methacrylic acid (%) |
|---|---|---|---|---|---|---|---|
| 12 | $Pd_1P_5Bi_1Sb_1O_{16.5}$ | 0 | 1000 | 290 | 79.8 | 58.5 | 73.3 |
|  |  | 0 | 4000 | 300 | 71.5 | 50.2 | 70.2 |
|  |  | 60 | 4000 | 300 | 65.8 | 47.5 | 72.2 |
|  |  | 90 | 4000 | 300 | 64.1 | 45.4 | 70.8 |
| 13 | $Pd_1P_1Bi_{0.5}Sb_1O_{5.75}$ | 0 | 1000 | 270 | 63.5 | 31.1 | 49.0 |
|  |  | 0 | 4000 | 280 | 61.0 | 29.0 | 47.5 |
|  |  | 60 | 4000 | 280 | 55.9 | 27.0 | 48.3 |
|  |  | 90 | 4000 | 280 | 54.3 | 26.6 | 49.0 |
| 14 | $Pd_1P_{1.5}Bi_1Sb_1O_{6.3}$ | 0 | 1000 | 270 | 64.0 | 32.5 | 50.8 |
|  |  | 0 | 4000 | 280 | 61.0 | 29.5 | 48.4 |
|  |  | 60 | 4000 | 280 | 54.2 | 25.9 | 47.8 |
|  |  | 90 | 4000 | 280 | 54.2 | 25.4 | 46.9 |
| 15 | $Pd_1P_3Bi_1Sb_1O_{10}$ | 0 | 1000 | 275 | 71.5 | 47.5 | 66.4 |
|  |  | 0 | 4000 | 284 | 67.0 | 41.5 | 61.9 |
|  |  | 60 | 4000 | 284 | 58.9 | 37.3 | 63.3 |
|  |  | 90 | 4000 | 284 | 57.1 | 36.0 | 63.0 |
| 16 | $Pd_1P_5Bi_3Sb_1O_{19.5}$ | 0 | 1000 | 295 | 76.1 | 53.5 | 70.3 |
|  |  | 0 | 4000 | 307 | 71.1 | 49.7 | 70.0 |
|  |  | 60 | 4000 | 307 | 67.4 | 47.7 | 70.8 |
|  |  | 90 | 4000 | 307 | 63.1 | 45.0 | 71.3 |
| 17 | $Pd_1P_8Bi_7Sb_5O_{39}$ | 0 | 1000 | 315 | 63.0 | 35.1 | 55.7 |
|  |  | 0 | 4000 | 320 | 61.0 | 30.8 | 50.5 |
|  |  | 60 | 4000 | 320 | 57.1 | 29.3 | 51.3 |
|  |  | 90 | 4000 | 320 | 55.2 | 28.2 | 51.1 |
| 18 | $Pd_1P_{28}Bi_{10}Sb_8O_{118}$ | 0 | 1000 | 328 | 57.5 | 30.5 | 53.0 |
|  |  | 0 | 4000 | 335 | 52.1 | 27.5 | 52.9 |
|  |  | 60 | 4000 | 335 | 47.4 | 24.3 | 51.3 |
|  |  | 90 | 4000 | 335 | 45.5 | 23.0 | 50.6 |
| 19 | $Pd_1P_5Bi_1Sb_{0.2}O_{15.3}$ | 0 | 1000 | 269 | 61.3 | 38.7 | 63.1 |
|  |  | 0 | 4000 | 280 | 58.8 | 32.2 | 54.8 |
|  |  | 60 | 4000 | 280 | 54.8 | 29.1 | 53.1 |
|  |  | 90 | 4000 | 280 | 52.1 | 27.9 | 53.6 |
| 20 | $Pd_1P_5Pb_1Sb_{0.5}O_{15.3}$ | 0 | 1000 | 280 | 59.5 | 48.5 | 81.5 |
|  |  | 0 | 4000 | 291 | 56.0 | 45.0 | 80.4 |
|  |  | 60 | 4000 | 291 | 53.6 | 41.7 | 77.8 |
|  |  | 90 | 4000 | 291 | 51.8 | 39.8 | 76.8 |
| 21 | $Pd_1P_5Pb_1Sb_1O_{16}$ | 0 | 1000 | 290 | 77.8 | 56.5 | 72.6 |
|  |  | 0 | 4000 | 300 | 72.0 | 51.0 | 70.8 |
|  |  | 60 | 4000 | 300 | 70.5 | 48.3 | 68.5 |
|  |  | 90 | 4000 | 300 | 67.5 | 46.4 | 68.7 |
| 22 | $Pd_1P_{15}Pb_8Sb_6O_{65.5}$ | 0 | 1000 | 300 | 55.4 | 39.5 | 71.3 |
|  |  | 0 | 4000 | 317 | 49.0 | 33.0 | 67.4 |
|  |  | 60 | 4000 | 317 | 47.0 | 30.7 | 65.3 |
|  |  | 90 | 4000 | 317 | 45.7 | 29.6 | 64.7 |
| 23 | $Pd_1P_1Pb_2Sb_{10}O_{20.5}$ | 0 | 1000 | 270 | 54.5 | 32.5 | 59.6 |
|  |  | 0 | 4000 | 282 | 51.1 | 29.1 | 57.0 |
|  |  | 60 | 4000 | 282 | 49.4 | 27.0 | 54.6 |
|  |  | 90 | 4000 | 282 | 50.0 | 27.3 | 54.6 |
| 24 | $Pd_1P_3Cr_1Sb_1O_{10}$ | 0 | 1000 | 265 | 57.5 | 31.1 | 54.1 |
|  |  | 0 | 4000 | 272 | 51.1 | 27.5 | 53.8 |
|  |  | 60 | 4000 | 272 | 46.8 | 25.4 | 54.3 |
|  |  | 90 | 4000 | 272 | 48.2 | 25.6 | 53.6 |
| 25 | $Pd_1P_5Cr_1Sb_1O_{16.5}$ | 0 | 1000 | 270 | 70.5 | 47.0 | 66.7 |
|  |  | 0 | 4000 | 285 | 67.5 | 42.1 | 62.4 |
|  |  | 60 | 4000 | 285 | 62.9 | 39.3 | 62.5 |
|  |  | 90 | 4000 | 285 | 62.3 | 38.9 | 62.4 |
| 26 | $Pd_1P_{18}Cr_7Sb_6O_{65.5}$ | 0 | 1000 | 300 | 55.8 | 32.1 | 57.5 |
|  |  | 0 | 4000 | 311 | 51.3 | 29.1 | 56.7 |
|  |  | 60 | 4000 | 311 | 49.3 | 27.3 | 55.4 |
|  |  | 90 | 4000 | 311 | 49.9 | 27.2 | 54.5 |
| 27 | $Pd_1P_2Ni_1Sb_1O_{8.5}$ | 0 | 1000 | 260 | 57.5 | 34.3 | 59.7 |
|  |  | 0 | 4000 | 273 | 53.0 | 31.1 | 58.7 |
|  |  | 60 | 4000 | 273 | 50.2 | 28.3 | 56.4 |
|  |  | 90 | 4000 | 273 | 48.6 | 27.6 | 56.8 |
| 28 | $Pd_1P_5Ni_1Sb_1O_{16}$ | 0 | 1000 | 270 | 76.5 | 51.5 | 67.3 |
|  |  | 0 | 4000 | 281 | 72.1 | 47.8 | 66.3 |
|  |  | 60 | 4000 | 281 | 68.5 | 44.7 | 65.3 |
|  |  | 90 | 4000 | 281 | 68.2 | 43.9 | 64.4 |
| 29 | $Pd_1P_3Ni_8Sb_7O_{27}$ | 0 | 1000 | 285 | 69.5 | 40.3 | 58.0 |
|  |  | 0 | 4000 | 300 | 63.0 | 32.5 | 51.6 |
|  |  | 60 | 4000 | 300 | 58.9 | 28.8 | 48.9 |
|  |  | 90 | 4000 | 300 | 57.9 | 27.8 | 48.0 |
| 30 | $Pd_1P_3Co_1Sb_1O_{11}$ | 0 | 1000 | 270 | 72.1 | 45.6 | 63.2 |
|  |  | 0 | 4000 | 285 | 69.0 | 41.3 | 59.9 |
|  |  | 60 | 4000 | 285 | 62.0 | 35.6 | 57.4 |
|  |  | 90 | 4000 | 285 | 60.8 | 34.9 | 57.4 |
| 31 | $Pd_1P_5Co_1Sb_1O_{16}$ | 0 | 1000 | 285 | 79.6 | 50.3 | 63.2 |
|  |  | 0 | 4000 | 297 | 73.5 | 48.8 | 66.4 |
|  |  | 60 | 4000 | 297 | 65.2 | 42.6 | 65.3 |
|  |  | 90 | 4000 | 297 | 64.8 | 40.9 | 63.1 |
| 32 | $Pd_1P_{25}Co_{10}Sb_7O_{84}$ | 0 | 1000 | 295 | 61.1 | 34.0 | 55.6 |
|  |  | 0 | 4000 | 303 | 57.7 | 32.1 | 55.6 |
|  |  | 60 | 4000 | 303 | 52.9 | 27.4 | 51.8 |
|  |  | 90 | 4000 | 303 | 53.7 | 28.1 | 52.3 |
| 33 | $Pd_1P_2Mn_1Sb_1O_{8.5}$ | 0 | 1000 | 255 | 60.0 | 30.5 | 50.8 |
|  |  | 0 | 4000 | 260 | 57.5 | 23.5 | 40.9 |
|  |  | 60 | 4000 | 260 | 57.6 | 22.3 | 38.7 |
|  |  | 90 | 4000 | 260 | 58.0 | 22.0 | 37.9 |
| 34 | $Pd_1P_5Mn_1Sb_1O_{16}$ | 0 | 1000 | 265 | 71.1 | 43.5 | 61.2 |

Table 2-continued

| Ex. No. | Catalyst composition | Lapse of time (days) | SV (hr$^{-1}$) | Temperature of nitrate bath (°C) | Conversion of methacrolein (%) | Yield of methacrylic acid (%) | Selectivity to methacrylic acid (%) |
|---|---|---|---|---|---|---|---|
|  |  | 0 | 4000 | 270 | 70.0 | 40.1 | 57.3 |
|  |  | 60 | 4000 | 270 | 67.3 | 36.4 | 54.1 |
|  |  | 90 | 4000 | 270 | 65.0 | 34.2 | 52.6 |
| 35 | $Pd_1P_6Mn_3Sb_4O_{25}$ | 0 | 1000 | 278 | 69.3 | 44.5 | 64.2 |
|  |  | 0 | 4000 | 289 | 65.5 | 40.9 | 62.4 |
|  |  | 60 | 4000 | 289 | 65.1 | 37.0 | 56.8 |
|  |  | 90 | 4000 | 289 | 63.6 | 34.6 | 54.4 |
| 36 | $Pd_1P_5Sn_{0.5}Sb_1O_{15.5}$ | 0 | 1000 | 265 | 71.1 | 48.0 | 67.5 |
|  |  | 0 | 4000 | 273 | 68.5 | 43.2 | 63.1 |
|  |  | 60 | 4000 | 273 | 61.5 | 39.3 | 63.9 |
|  |  | 90 | 4000 | 273 | 59.7 | 38.4 | 64.3 |
| 37 | $Pd_1P_2Sn_1Sb_1O_{8.5}$ | 0 | 1000 | 265 | 73.0 | 44.0 | 60.3 |
|  |  | 0 | 4000 | 275 | 68.0 | 42.9 | 63.1 |
|  |  | 60 | 4000 | 275 | 61.0 | 38.4 | 63.0 |
|  |  | 90 | 4000 | 275 | 59.0 | 38.0 | 64.4 |
| 38 | $Pd_1P_5Sn_1Sb_1O_{16}$ | 0 | 1000 | 275 | 78.5 | 53.1 | 67.6 |
|  |  | 0 | 4000 | 284 | 72.5 | 51.1 | 70.5 |
|  |  | 60 | 4000 | 284 | 69.7 | 47.6 | 68.3 |
|  |  | 90 | 4000 | 284 | 69.1 | 47.0 | 68.0 |
| 39 | $Pd_1P_{15}Sn_9Sb_3O_{52}$ | 0 | 1000 | 285 | 57.1 | 33.5 | 58.7 |
|  |  | 0 | 4000 | 298 | 56.0 | 29.1 | 52.0 |
|  |  | 60 | 4000 | 298 | 52.7 | 27.3 | 51.8 |
|  |  | 90 | 4000 | 298 | 52.7 | 27.7 | 52.6 |
| 40 | $Pd_1P_2U_{0.5}Sb_{0.3}O_8$ | 0 | 1000 | 265 | 69.5 | 41.1 | 59.1 |
|  |  | 0 | 4000 | 275 | 65.0 | 37.5 | 57.7 |
|  |  | 60 | 4000 | 275 | 61.2 | 34.8 | 56.9 |
|  |  | 90 | 4000 | 275 | 59.7 | 34.2 | 57.3 |
| 41 | $Pd_1P_5U_1Sb_1O_{18}$ | 0 | 1000 | 270 | 73.1 | 49.5 | 67.7 |
|  |  | 0 | 4000 | 288 | 71.5 | 43.3 | 60.6 |
|  |  | 60 | 4000 | 288 | 69.1 | 40.0 | 57.9 |
|  |  | 90 | 4000 | 288 | 70.2 | 39.8 | 56.7 |
| 42 | $Pd_1P_{10}U_1Sb_3O_{33.5}$ | 0 | 1000 | 290 | 61.5 | 32.5 | 52.8 |
|  |  | 0 | 4000 | 302 | 57.0 | 27.6 | 48.4 |
|  |  | 60 | 4000 | 302 | 52.7 | 24.6 | 46.7 |
|  |  | 90 | 4000 | 302 | 50.5 | 23.2 | 45.9 |
| 43 | $Pd_1P_5Ba_{0.2}Sb_1O_{15.2}$ | 0 | 1000 | 271 | 59.5 | 43.5 | 73.1 |
|  |  | 0 | 4000 | 287 | 54.6 | 40.1 | 73.4 |
|  |  | 60 | 4000 | 287 | 51.5 | 36.2 | 70.3 |
|  |  | 90 | 4000 | 287 | 51.7 | 35.6 | 68.8 |
| 44 | $Pd_1P_5Ba_1Sb_1O_{16}$ | 0 | 1000 | 289 | 64.3 | 51.2 | 79.6 |
|  |  | 0 | 4000 | 300 | 62.1 | 47.5 | 76.5 |
|  |  | 60 | 4000 | 300 | 58.8 | 43.2 | 73.5 |
|  |  | 90 | 4000 | 300 | 55.6 | 40.6 | 73.0 |
| 45 | $Pd_1P_3Ba_{1.5}Sb_6O_{19}$ | 0 | 1000 | 275 | 60.5 | 35.3 | 58.3 |
|  |  | 0 | 4000 | 287 | 58.8 | 31.5 | 53.6 |
|  |  | 60 | 4000 | 287 | 53.4 | 27.6 | 51.7 |
|  |  | 90 | 4000 | 287 | 52.6 | 26.3 | 50.0 |
| 46 | $Pd_1P_2Fe_1Sb_1O_9$ | 0 | 1000 | 265 | 65.5 | 35.5 | 54.2 |
|  |  | 0 | 4000 | 277 | 62.5 | 30.7 | 49.1 |
|  |  | 60 | 4000 | 277 | 58.2 | 28.7 | 49.3 |
|  |  | 90 | 4000 | 277 | 55.4 | 26.5 | 47.8 |
| 47 | $Pd_1P_5Fe_1Sb_1O_{16.5}$ | 0 | 1000 | 287 | 70.5 | 49.5 | 70.2 |
|  |  | 0 | 4000 | 300 | 65.2 | 43.1 | 66.1 |
|  |  | 60 | 4000 | 300 | 63.0 | 40.4 | 64.1 |
|  |  | 90 | 4000 | 300 | 59.3 | 38.9 | 65.6 |
| 48 | $Pd_1P_6Fe_7Sb_{10}O_{41.5}$ | 0 | 1000 | 290 | 62.1 | 31.1 | 50.1 |
|  |  | 0 | 4000 | 299 | 60.0 | 27.9 | 46.5 |
|  |  | 60 | 4000 | 299 | 54.6 | 25.0 | 45.8 |
|  |  | 90 | 4000 | 299 | 56.4 | 24.3 | 43.1 |
| 49 | $Pd_1P_5Sb_1Bi_{0.5}Pb_{0.5}O_{15}$ | 0 | 4000 | 300 | 70.5 | 50.0 | 70.9 |
|  |  | 60 | 4000 | 300 | 68.1 | 47.5 | 69.8 |
|  |  | 90 | 4000 | 300 | 66.7 | 46.7 | 70.0 |
| 50 | $Pb_1P_5Sb_1Ba_{0.5}Fe_{0.5}O_{15.25}$ | 0 | 4000 | 299 | 71.5 | 50.3 | 70.4 |
|  |  | 60 | 4000 | 299 | 66.4 | 46.5 | 70.1 |
|  |  | 90 | 4000 | 299 | 65.0 | 45.6 | 70.1 |

COMPARATIVE EXAMPLES 1 - 3

By following the procedure of Example 3 of Japanese Patent Laid Open Publication No. 61416/1973, a catalyst comprising molybdenum, phosphorus, thallium and silicon in an atomic ratio of 1 : 0.08 : 0.16 : 0.08 was prepared. To be specific, 237 g of phosphomolybdic acid were dissolved with heating in 400 ml of water. To the resultant solution, an aqueous solution obtained by adding dropwise 17.0 g of silicon tetrachloride with simultaneous agitation into 200 ml of ice water was added and heated. Further, an aqueous solution obtained by dissolving 53.2 g of thallium nitrate with heating into 200 ml of water was added thereto. The resultant mixture and 50 ml of a 28% aqueous ammonia solution were mixed and, while agitated, evaporated to dryness. The dry product was calcined in a muffle furnace at 450° C for five hours, then pulverized and thereafter, molded to produce a catalyst in the form of tablets.

By following the procedure of Example 3 of Japanese Patent Laid Open Publication No. 61417/1973, a catalyst comprising molybdenum, phosphorus, rubidium and silicon in an atomic ratio of 1 : 0.08 : 0.16 : 0.08 was prepared. To be specific, 237 g of phosphomolybdic acid were dissolved with heating in 400 ml of water. To the resultant solution, an aqueous solution obtained by adding dropwise 17.0 g of silicon tetrachloride with simultaneous agitation into 200 ml of ice water was added and heated. Further, an aqueous solution obtained by dissolving 29.5 g of rubidium nitrate with heating into 200 ml of water was added thereto. The resultant mixture and 50 ml of a 28% aqueous ammonia solution were mixed and thereafter, while agitated, evaporated to dryness. The dry product was calcined in a muffle furnace at 450° C for five hours, then pulverized and thereafter, molded to produce a catalyst in the form of tablets.

A catalyst comprising molybdenum, phosphorus, cesium and chromiun in an atomic ratio of 1 : 0.16 : 0.16 : 0.16 was prepared by following the procedure of Example 1 of Japanese Patent Laid Open Publication No. 67216/1973. To be specific, 237 g of phosphomolybdic acid were dissolved with heating in 300 ml of water. To the resultant solution, an aqueous solution having 20 g of chromic anhydride dissolved in 100 ml of water was added and agitated. Further, an aqueous solution having 11.5 g of 85% phosphoric acid dissolved in 100 ml of water and an aqueous solution having 39.0 of cesium nitrate dissolved with heating in 200 ml of water were added thereto. The resultant mixture and 100 ml of a 28% aqueous ammonia solution were mixed and while agitated, evaporated to dryness. The dry product was calcined in a muffle furnace at 450° C for 16 hours, then pulverized and thereafter, molded into a catalyst in the form of tablets.

The three catalysts described above were used to effect the reaction by following the procedure of Example 1. The results of the reaction were as shown in Table 3.

Table 3

| Ex. No. | Catalyst composition | Lapse of time (days) | SV (hr$^{-1}$) | Temperature of nitrate bath (° C) | Conversion of methacrolein (%) | Yield of Methacrylic acid (%) | Selectivity to methacrylic acid (%) |
|---|---|---|---|---|---|---|---|
| 1 | $Mo_1P_{0.08}Tl_{0.16}Si_{0.08}$ | 0 | 4000 | 367 | 70.5 | 51.5 | 73.0 |
|  |  | 30 | 4000 | 367 | 63.5 | 48.7 | 76.7 |
|  |  | 60 | 4000 | 367 | 48.5 | 32.5 | 67.0 |
|  |  | 90 | 4000 | 367 | 35.5 | 19.8 | 55.8 |
| 2 | $Mo_1P_{0.08}Rb_{0.16}Si_{0.08}$ | 0 | 4000 | 367 | 70.9 | 50.1 | 70.7 |
|  |  | 30 | 4000 | 367 | 62.6 | 47.3 | 75.6 |
|  |  | 60 | 4000 | 367 | 44.5 | 30.5 | 68.5 |
|  |  | 90 | 4000 | 367 | 34.7 | 18.1 | 52.2 |
| 3 | $Mo_1P_{0.16}Cs_{0.16}Cr_{0.16}$ | 0 | 4000 | 358 | 63.5 | 51.5 | 81.1 |
|  |  | 30 | 4000 | 358 | 57.3 | 46.5 | 81.2 |
|  |  | 60 | 4000 | 358 | 39.5 | 30.1 | 76.2 |
|  |  | 90 | 4000 | 358 | 31.3 | 19.2 | 61.3 |

It is clear from the results shown above that the conventional Mo-P type catalysts have a short lifetime as catalysts and that when they are used for a long time in the oxidation reaction of methacrolein, they suffer significant losses in activity.

In contrast, the catalysts of the present invention enjoy a very long catalyst life.

EXAMPLE 51

When raw feed gas consisting of methacrolein, oxygen, steam and nitrogen in a molar ratio of 1 : 4.2 : 2 : 16.9 was used in Example 1, nearly the same results as in Example 1 were obtained.

EXAMPLE 52

When raw feed gas consisting of methacrolein, oxygen, steam and nitrogen in a molar ratio of 1 : 4.2 : 4 : 16.9 was used in Example 1, nearly the same results as in Example 1 were obtained.

What is claimed is:

1. A catalyst having the following composition:

$$Pd_aP_bSb_cX_dO_e$$

wherein, Pd, P, Sb and O denote palladium, phosphorus, antimony and oxygen, respectively, X denotes at least one element selected from the group consisting of bismuth, lead, chromium, iron, nickel, cobalt, manganese, tin, uranium and barium, the subscripts $a$, $b$, $c$, $d$ and $e$ denote the numbers of the Pd, P, Sb, X and O atoms with the proviso that the elements are present in a ratio so that when $a$ is 1, then $b$ is 1 to 42, $c$ is 0.1 to 15, $d$ is 0 to 15 and $e$ is automatically determined from the valencies of the other elements.

2. The catalyst according to claim 1, wherein $b$ is from 1 to 28, $c$ is 0.3 to 10, $d$ is 0 to 10 and $e$ is 5 to 85 when $a$ is 1.

3. The catalyst according to claim 1, wherein X is bismuth.

4. The catalyst according to claim 1, wherein X is lead.

5. The catalyst according to claim 22, wherein X is barium.

6. A method of manufacturing methacrylic acid by the oxidation of methacrolein with molecular oxygen or a gas containing molecular oxygen in the presence of steam, which method is characterized by using a catalyst having the following composition:

$$Pd_aP_bSb_cX_dO_e$$

wherein, Pd, P, Sb and O denote palladium, phosphorus, antimony and oxygen respectively, X denotes at least one element selected from the group consisting of bismuth, lead, chromium, iron, nickel, cobalt, manganese, tin, uranium and barium, the subscripts $a$, $b$, $c$, $d$ and $e$ denote the numbers of the pd, P, Sb, X and O atoms, with the proviso that the elements are present in a ratio so that when $a$ is 1, $b$ is 1 to 42, $c$ is 0.1 to 15, $d$ is 0 to 15 and $e$ is a value which is automatically determined from the valencies of the other elements.

7. The method according to claim 6, wherein $b$ is 1 to 28, $c$ is 0.3 to 10, $d$ is 0 to 10 and $e$ is 5 to 85 when $a$ is 1.

8. The method according to claim 6, wherein X is bismuth.

9. The method according to claim 6, wherein X is lead.

10. The method according to claim 6, wherein X is barium.

UNITED STATES PATENT OFFICE
CERTIFICATE OF CORRECTION

Patent No. 4,042,623　　　　　　　　　Dated　August 16, 1977

Inventor(s)　MASANOBU OGAWA

It is certified that error appears in the above-identified patent and that said Letters Patent are hereby corrected as shown below:

Column 1, line 19, after "to" insert --the--.

Column 4, line 37, above "carbon" insert --Yield--.

Column 5, line 7, change "direction" to --reaction--.

Column 6, line 53, delete "for".

Column 11, line 19, after "39.0" insert --g--.

Column 12, line 22, change "22" to --1--.

Signed and Sealed this

Twenty-second Day of November 1977

[SEAL]

Attest:

RUTH C. MASON　　　　　　　　LUTRELLE F. PARKER
Attesting Officer　　　　　Acting Commissioner of Patents and Trademarks